(12) United States Patent
Takahashi et al.

(10) Patent No.: US 10,377,902 B2
(45) Date of Patent: Aug. 13, 2019

(54) CRYSTALLIZED RED PIGMENT, METHOD OF PRODUCING A RECRYSTALLIZED RED PIGMENT AND A METHOD FOR IMPROVING THE APPEARANCE OF OR PREVENTING WRINKLES

(71) Applicants: HEIMAT CO., LTD., Tokyo (JP); Masao Takahashi, Tokyo (JP); TOKIWA PHYTOCHEMICAL CO., LTD., Chiba (JP)

(72) Inventors: Masao Takahashi, Tokyo (JP); Nobuhito Kimura, Chiba (JP)

(73) Assignees: HEIMAT CO., LTD., Tokyo (JP); MASAO TAKAHASHI, Tokyo (JP); TOKIWA PHYTOCHEMICAL CO., LTD., Chiba (JP)

( * ) Notice: Subject to any disclaimer, the term of this patent is extended or adjusted under 35 U.S.C. 154(b) by 917 days.

(21) Appl. No.: 14/786,748

(22) PCT Filed: Oct. 4, 2013

(86) PCT No.: PCT/JP2013/077148
§ 371 (c)(1),
(2) Date: Mar. 4, 2016

(87) PCT Pub. No.: WO2014/174703
PCT Pub. Date: Oct. 30, 2014

(65) Prior Publication Data
US 2016/0297971 A1    Oct. 13, 2016

(30) Foreign Application Priority Data

Apr. 26, 2013 (CN) .......................... 2013 1 0150798

(51) Int. Cl.
| | | |
|---|---|---|
| *A61K 36/00* | (2006.01) | |
| *C09B 61/00* | (2006.01) | |
| *A61Q 19/08* | (2006.01) | |
| *A61K 8/97* | (2017.01) | |
| *A61K 31/352* | (2006.01) | |
| *A61K 36/889* | (2006.01) | |
| *C09B 57/02* | (2006.01) | |
| *C09B 67/46* | (2006.01) | |
| *A23L 5/42* | (2016.01) | |
| *A23L 33/105* | (2016.01) | |
| *A61K 8/49* | (2006.01) | |
| *A61K 31/353* | (2006.01) | |

(52) U.S. Cl.
CPC .............. *C09B 61/00* (2013.01); *A23L 5/42* (2016.08); *A23L 33/105* (2016.08); *A61K 8/498* (2013.01); *A61K 8/97* (2013.01); *A61K 31/352* (2013.01); *A61K 31/353* (2013.01); *A61K 36/889* (2013.01); *A61Q 19/08* (2013.01); *C09B 57/02* (2013.01); *C09B 67/0091* (2013.01); *A61K 2236/00* (2013.01); *A61K 2236/33* (2013.01); *A61K 2236/51* (2013.01); *A61K 2236/55* (2013.01); *A61K 2800/43* (2013.01)

(58) Field of Classification Search
CPC ........................................................ A61K 36/00
USPC .......................................................... 424/725
See application file for complete search history.

(56) References Cited

U.S. PATENT DOCUMENTS

| | | |
|---|---|---|
| 2005/0271751 A1 | 12/2005 | Perrier et al. |
| 2009/0004302 A1 | 1/2009 | Cyr |
| 2010/0047361 A1 | 2/2010 | Perrier et al. |
| 2010/0323041 A1 | 12/2010 | Cyr |
| 2011/0117218 A1* | 5/2011 | Schmidt .................. A61K 8/63 424/727 |

FOREIGN PATENT DOCUMENTS

| | | |
|---|---|---|
| JP | 2007230888 A | 9/2007 |
| JP | 2008516899 A | 5/2008 |
| JP | 2009292846 A | 12/2009 |
| JP | 2012171876 A | 9/2012 |
| JP | 2012171877 A | 9/2012 |
| JP | 2013139432 A | 7/2013 |

OTHER PUBLICATIONS

International Preliminary Report on Patentability (IPRP) including Written Opinion dated Oct. 27, 2015, issued in counterpart International Application No. PCT/JP2013/077148.
International Search Report (ISR) dated Nov. 12, 2013, issued in counterpart International Application No. PCT/JP2013/077148.
"Material Safety Data Sheet—Saw Palmetto Extract", http://www.sawpalmetto.com/lib/datasheet/index.html.
Chung, et al., "Angiogenesis in skin aging and photoaging", Journal of Dermatology; 2007; 34 (9); pp. 593-600.
Kawada, et al., "Increased oxygen tension attenuates acute ultraviolet-B-induced skin angiogenesis and wrinkle formation", American Journal of Physiology: Regulatory, Integrative and Comparative Physiology; 2010; 299; pp. R694-R701.
Plosker, et al., "Serena repens (Permixon): A Review of its Pharmacology and Therapeutic Efficacy in Benign Prostatic Hyperplasia", Drugs & Aging; Nov. 1996; 9 (5); pp. 379-395.
Yano, et al., "Targeted Overexpression of the Angiogenesis Inhibitor Thrombospondin-1 in the Epidermis of Transgenic Mice Prevents Ultraviolet-B-Induced Angiogenesis and Cutaneous Photo-Damage", Journal of Investigative Dermatology; 2002; 118 (5); pp. 800-805.
Yano, et al., "Ultraviolet B-Induced Skin Angiogenesis is Associated with a Switch in the Balance of Vascular Endothelial Growth Factor and Thrombospondin-1 Expression", The Journal of Investigative Dermatology; 2004; 122 (1); pp. 201-208.

* cited by examiner

Primary Examiner — Michael V Meller
(74) Attorney, Agent, or Firm — Holtz, Holtz & Volek PC

(57) ABSTRACT

A crystalized red pigment of saw palmetto fruit obtained by extracting a saw palmetto fruit with ethanol and depositing a red pigment in the extract.

2 Claims, 7 Drawing Sheets

(A)

(B)

1. Saw palmetto (before hydrolysis)
2. Saw palmetto (after hydrolysis)
3. Cyanidin
4. Delphinidin
5. Peonidin
6. Petunidin
7. Malvidin R=H, OH
n=1 or or more

CRYSTALLIZED RED PIGMENT, METHOD OF PRODUCING A RECRYSTALLIZED RED PIGMENT AND A METHOD FOR IMPROVING THE APPEARANCE OF OR PREVENTING WRINKLES

TECHNICAL FIELD

The present invention is related to an anti-angiogenesis agent comprising an extract or a red pigment from saw palmetto fruit. Further, the present invention is related to a method of producing the extract.

BACKGROUND ART

Saw palmetto is used in a Chinese herbal medicine for urologic disease from old times. In addition, it has been suggested for an action such as a tonic, a diuretic and anti-prostatomegaly. These effects derive from saw palmetto fruit or oil ingredients thereof (Non-patent documents 1 and 2).

Angiogenesis means the proliferation and growth of new blood vessels. Angiogenesis plays an important role in several physiological and pathological conditions.

In a healthy body, angiogenesis is caused in a growth phase in wound healing, for recovery of blood flow to a wound tissue, and at duration of the menstruation or pregnancy.

With over exposure of the skin to UV-rays, it is known that a thicker microvessel involved in wrinkle formation is increased abnormally thereby a research for an anti-angiogenic agent for the prevention or treatment of wrinkle has been conducted (Non-patent documents 3 to 6).

A lack of control of angiogenesis causes a number of severe disorders. It is known that so-called "overexpression of angiogenesis" causes a number of disorders. They are involved in psoriasis, arthritis, retinopathy, glaucoma, macular degeneration, periodontal disease and cancer. For example, a cancer has a high turnover efficiency compared with a normal growth of tissue. As a cancer requires more blood flow for obtaining a higher nutritional supply, anti-angiogenesis could be one of useful mechanisms for suppressing or controlling a cancer. Thus an anti-angiogenesis factor can delay the progress of such diseases.

PRIOR ART DOCUMENTS

Non-patent Documents

Non-patent document 1: Plosker G L, Brogden R N. Serenoarepens (Permixon). A review of its pharmacology and therapeutic efficacy in benign prostatic hyperplasia.Drugs Aging. 1996 Nov; 9 (5): 379-95.

Non-patent document 2: http://www.sawpalmetto.com/lib/datasheet/index.html Non-patent document 3: Chung J H, Eun H C. Angiogenesis in skin aging and photoaging. JDermatol. 2007; 34 (9): 593-600.

Non-patent document 4: Yano K, Kajiya K, Ishiwata M, Hong Y K, Miyakawa T, Detmar M. Ultraviolet B-induced skin angiogenesis is associated with a switch in the balance of vascular endothelial growth factor and thrombospondin-1 expression. J Invest Dermatol. 2004; 122 (1): 201-8.

Non-patent document 5: Shigeo Kawada, Masaru Ohtani, and Naokata Ishii. Increased oxygen tension attenuates acute ultraviolet-B-induced skin angiogenesis and wrinkle formation. Am J PhysiolRegulIntegr Comp Physiol 2010; 299: R694-R701.

Non-patent document 6: Kiichiro Yano, HajimuOura, and Michael Detmar. Targeted overexpression of the angiogenesis Inhibitor thrombospondin-1 in the epidermis of transgenic mice prevents ultraviolet-B-induced angiogenesis and cutaneous photo-damage. J Invest Dermatol 2002; 118:800-805. J Invest Dermatol 118: 800-805, 2002.

DISCLOSURE OF THE INVENTION

Problems to be Solved by the Invention

The problem of the present invention is to provide an anti-angiogenesis agent comprising an ethanol extract or red pigment. Further, the problem of the present invention is to provide a method of producing a red pigment from an ethanol extract of saw palmetto and an anti-angiogenesis agent comprising the red pigment.

Means for Solving the Problems

The inventor found that the an ethanol extract of saw palmetto fruit has a marked action for preventing angiogenesis and the inventor establish a purification method for a red pigment of saw palmetto fruit from an ethanol extract. And the inventor found that the red pigment has a marked action for preventing angiogenesis, thereby the inventor made the present invention.

Accordingly:
(1) the invention relates to an anti-angiogenesis agent, comprising an ethanol extract or a red pigment of saw palmetto fruit;
(2) the invention relates to a cosmetic, comprising the anti-angiogenesis agent according to the above (1);
(3) the invention relates to the cosmetic according to the above (2), for improving or preventing wrinkles;
(4) the invention relates to a medicine, comprising the anti-angiogenesis agent according to the above (1);
(5) the invention relates to the medicine according to the above (4) for treating or preventing a disease or disorder that suppressing angiogenesis is beneficial;
(6) the invention relates to a method of producing the anti-angiogenesis agent according to the above (1), comprising extracting a saw palmetto fruit with ethanol;
(7) the invention relates to a method of producing the cosmetic according to the above (2) or (3), comprising extracting a saw palmetto fruit with ethanol;
(8) the invention relates to a method of producing the medicine according to the above (4) or (5), comprising extracting a saw palmetto fruit with ethanol;
(9) the invention relates to a crystalized red pigment derived from a saw palmetto fruit;
(10) the invention relates to the crystalized red pigment according to the above (9), obtained by extracting a saw palmetto fruit with ethanol and depositing a red pigment in the extract;
(11) the invention relates to the crystalized red pigment fruit according to the above (9) or (10), wherein the crystalize red pigment comprises proanthocyanidin derived from a saw palmetto;
(12) the invention relates to a composition, comprising the red pigment according to the above (9) or (10);
(13) the invention relates to an anti-angiogenesis agent, comprising the crystalized red pigment according to the above (9) or (10);
(14) the invention relates to a food, comprising the crystalized red pigment according to the above (9) or (10), the composition according to the above (12), or the anti-angiogenesis agent according to the above (13);

(15) the invention relates to a cosmetic, comprising the crystalized red pigment according to the above (9) or (10), the composition according to the above (12), or the anti-angiogenesis agent according to the above (13);

(16) the invention relates to the cosmetic according to the above (15), for improving or preventing wrinkles;

(17) the invention relates to a medicine, comprising the crystalized red pigment according to the above (9) or (10), the composition according to the above (12), or the anti-angiogenesis agent according to the above (13);

(18) the invention relates to the medicine according to the above (17), for treating or preventing a disease or disorder that suppressing angiogenesis is beneficial;

(19) the invention relates to a method of producing the crystalized red pigment according to the above (9) or (10), comprising the following steps:
extracting a saw palmetto fruit with ethanol,
separating an extract from a solid residue,
concentrating the extract,
mixing the concentrate with water,
ultrasonicating the mixture to separate water layer from oil phase, and
recovering a red pigment deposited from water phase,

(20) the invention relates to a method for producing the composition according to the above (12), comprising the method for producing a crystalized red pigment according to the above (19);

(21) the invention relates to a method for producing the anti-angiogenesis agent according to the above (13), comprising the method for producing a crystalized red pigment according to the above (19);

(22) the invention relates to a method for producing the food according to the above (14), comprising the method for producing a crystalized red pigment according to the above (19);

(23) the invention relates to a method for producing the cosmetic according to the above (15) or (16), comprising the method for producing a crystalized red pigment according to the above (19);

(24) the invention relates to a method for producing the medicine according to the above (17) or (18), comprising the method for producing a crystalized red pigment according to the above (19);

(25) the invention relates to an anti-angiogenesis agent, comprising an ethanol extract or a red pigment of saw palmetto fruit, wherein an ethanol extract or red pigment of saw palmetto fruit is the crystalized red pigments according to the above (11);

(26) the invention relates to a composition, comprising the crystalized red pigments according to the above (11);

(27) the invention relates to a food, comprising the crystalized red pigments according to the above (11);

(28) the invention relates to a cosmetic, comprising the crystalized red pigments according to the above (11);

(29) the invention relates to a medicine, comprising the crystalized red pigments according to the above (11);

(30) the invention relates to a method of producing the crystalized red pigment according to the above (11), comprising the steps:
extracting a saw palmetto fruit with ethanol,
separating an extract from a solid residue,
concentrating the extract,
mixing the concentrate with water,
ultrasonicating the mixture to separate oil layer from water phase, and
recovering a red pigment deposited from water phase;

(31) the invention relates to a method of producing the composition according to the above (26), comprising the method of the above (30);

(32) the invention relates to a food of producing the composition according to the above (27), comprising the method of the above (30);

(33) the invention relates to a method of producing the cosmetic according to the above (28), comprising the method of the above (30);

(34) the invention relates to a method of producing the medicine according to the above (23), comprising the method of the above (30);

Effect of the Invention

This invention discovered a remarkable anti-angiogenesis action in an ethanol extract from saw palmetto fruit, and also a remarkable anti-angiogenesis action in a red pigment of saw palmetto fruit purified from the ethanol extract.

BEST MODE FOR CARRYING OUT THE INVENTION

Figure 1:
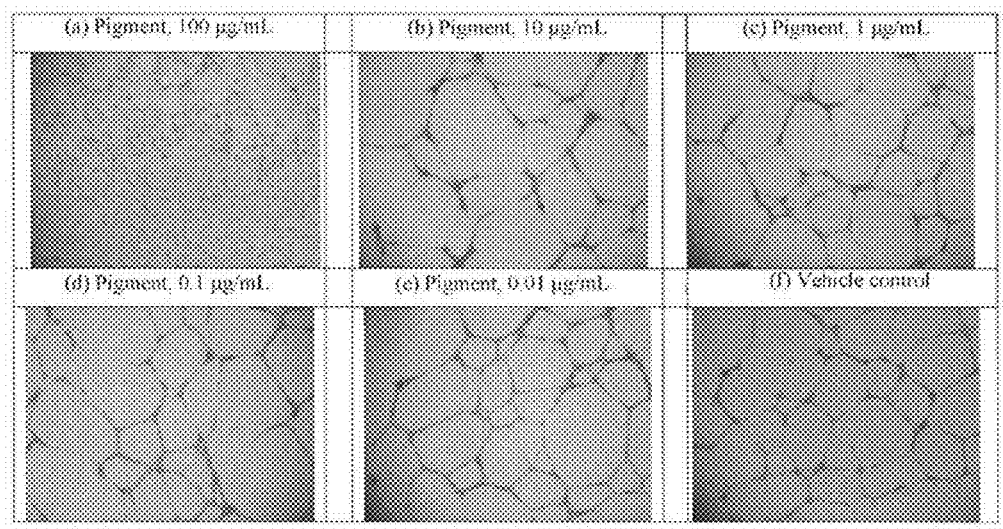
FIG. 1: A picture of tube formation under the presence of test substance to the HUVEC cell on the Matrigel.
(a): Effect of 100 μg/mL red pigment treatment for the tube formation. There is almost no tube formation. (b), (c), (d), (e): 10 μg/mL, 1ug/mL, 0.1 m/mL, 0.01 μg/mL of red pigment treatment. (f): Effect of vehicle control treatment for the tube formation. The whole length of the tube was measured from the picture. (g):
Effect of 30 μM suramin treatment for the tube formation. There is almost no tube formation. (h), (i), (j), (k): 15 μM, 10 μM, 3 μM, 1 μM of suramin treatment. (1): Vehicle control treatment.
The whole length of the tube was measured from the picture.
Figure 1:
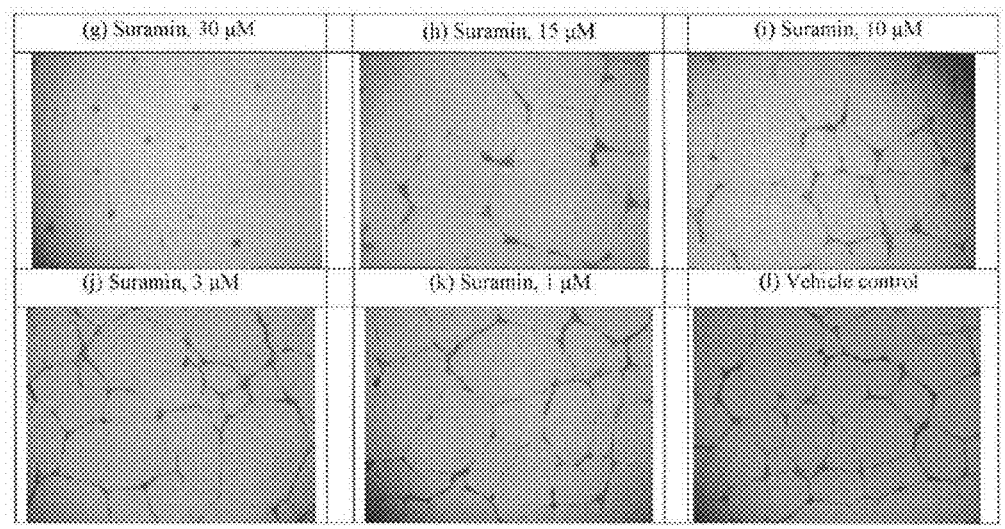

Saw palmetto fruit means the fruit belonging to the family Arecaceae genus Trachycarpus. Preferably, it is a fruit of Serenoa serrulate or Serenoa repens. The saw palmetto fruit was obtained from a market.

Preferably, a saw palmetto fruit is a dried saw palmetto fruit. The dried saw palmetto fruit contains, but not limited to, not more than 10% w/w of water, and preferably not more than 5% of water. The dried saw palmetto fruit can obtain from a fresh saw palmetto fruit by dehydrating and drying by using any methods (e.g., solar drying, heat drying, vacuum drying, vacuum-freeze drying). Preferably, the dried saw palmetto fruit is in a form of milling or powdering.

Ethanol includes, but not limited to a solvent including ethanol, preferably, it is aqueous ethanol including not less than 30%v/v ethanol. More preferably, it includes 80 to 100%v/v ethanol, and even more preferably, it includes 90 to 95%v/v/ ethanol.

An extraction of saw palmetto fruit with ethanol is conducted by adding ethanol to a saw palmetto fruit and stirring for a certain period of time at room temperature (15° C. to 28° C.) or under heating.

The extraction heating temperature may be below the boiling point of ethanol, or below 120° C. in an airtight container. A preferred extraction temperature is 90 to 100. More preferably, it is 95 to 105° C. A preferable heating method is, but not limited to, heating in an oil bath.

The extraction time is, but not limited to, from 5 min to 24hrs, preferably from 15 min. to 3hrs, more preferably from 30min. to 2hrs.

The extraction may be conducted, but not limited to, one or two times or more.

The extraction may be conducted, but not limited to, with stirring. The preferred stirring method was by use of a magnetic stirrer and stirring bar, or a motor driven stirrer. The agitation rate was generally, from 100 to 600 rpm but preferably from 200 to 500 rpm.

The used amount of ethanol to saw palmetto fruit in extraction is, but not limited to, 300 parts or more of ethanol, preferably 500 to 2000 ethanol and even preferably 750 to 1500 ethanol to 100 parts by weight of saw palmetto.

Alternatively, the water content of the mixture of saw palmetto fruit and ethanol in extraction is not more than 70% w/w, preferably less than 20% w/w and even preferably 10% w/w. In the case of the extraction for 100 g of dried saw palmetto fruit with 10% water and 1000 mL of 90% v/v ethanol (density is 0.8222 at 15° C., 90v/v % (according to International Organization of Legal Metrology (OIML))), the water content at extraction (%) was calculated as [weight of water in saw palmetto 10 g+weight of water in ethanol 100 g]/[weight of saw palmetto 100 g+weight of ethanol 822 g]*100=12%.

After the ethanol extraction, it is separated to an ethanol extract and a solid residue to obtain an ethanol extract. A separation method is preferably, but not limited to, filtration or centrifugation.

The filtration method for the ethanol extract is preferably, but not limited to, by using a membrane (nylon mesh, paper etc.), filter (Nutsche's filter, Buchner funnel etc.). In addition, combined use of both coarse filtration and fine filtration is preferable.

The pore size of the coarse filter is, but not limited to, 500 to 50 μm, preferably 300 to 100 μm.

The pore size of the fine filter is, but not limited to, 10 to 1 μm, preferably 7.5 to 2.5 μm and even preferably 6 to 4 μm. In addition, it was preferable to use celite or other diatomaceous earth overlaid on a filter paper as a filter aid.

The filtration method includes, but not limited to, natural dripping, pressure filtration or vacuum filtration. The filtration can be conducted one time or more.

The filtrate is preferably, but not limited to, concentrated. Preferably, concentration is conducted under low pressure. The concentration ratio is, but not limited to, doubled to inspissation, preferably triple to 30 times and more preferably 5 to 20 times.

The ethanol extract means the extract obtained by extracting of saw palmetto fruit with ethanol and separating solid residue, or concentration thereof. If the separation is conducted by filtration, filtration may be only coarse filtration.

Water is added to the concentrate and the mixture is stirred. The stirring method of the mixture and water is, but not limited to, preferably a combination of a magnetic stirrer and a stirring bar or a motor agitator. Agitating speed is, but not limited to, 100 to 600 rpm, preferably 200 to 500 rpm. Agitating time is, but not limited to, 1 to 60 min., preferably 3 to 30 min., and more preferably 5 to 15 min. Agitating temperature is, but not limited to, at 15 to 30° C., preferably at 20 to 25° C.

The mixture ratio of concentrate and water is more than 100 parts by weight of water, preferably 200 to 1000 parts by weight of water and even preferably 300 parts by weight to 500 parts by weight of water, to 100 parts by weight of concentrate.

The mixture of concentrate and water after stirring is ultra-sonicated. By ultra-sonicating the mixture, the mixture is separated to the oil layer and water layer and the red pigment in red color is crystalized and precipitated in the water layer. Accordingly, frequency, intensity, time and methods of ultrasonic waves, and ultrasonic generator were not limited.

Ultrasonic frequency is in the range 20 KHz to 1 MHz, preferably between 20 KHz to 100 KHz, and even preferably between 25 KHz to 50 KHz. Exposure time is in the range 10 seconds to 1 hour, preferably between 20 seconds to 30 minutes, and even preferably between 30 seconds to 5 minutes. Wave intensity is used, but not limited to, at the default value of the individual ultrasonic generator.

The ultrasonic generator includes, but not limited to, an ultrasonic generator with an oscillator or the ultrasonic cleaner. In the use of the oscillator, preferably the probe is immersed in the mixture to provide ultrasonic vibration. In the use of the ultrasonic cleaner, preferably the vessel containing the mixture is placed in the water within the ultrasonic cleaner. The use of the ultrasonic cleaner is preferable.

The water layer is separated and collected from the oil layer. The separation method is preferably, but not limited to, collecting water layer by using a separating funnel.

The crystal is collected from the water layer. The collection method is preferably, but not limited to, filtration or by centrifugation.

The filtration method for collecting the crystal, is conducted by using a filter membrane (nylon mesh, filter paper etc.), and strainer (Nutsche filter, and Buchner funnel). Pore size of filtration is, not be limited if it is a size possible for collecting a crystal, between10 to 1 µm, preferably between 7.5 to 2.5 µm, and more preferably between 6 to 4 µm. Filtration method is, not be limited to, natural dripping, pressure filtration or vacuum filtration. Preferably, it is vacuum filtration.

The collected crystal is preferably rinsed residual fat after filtration off using water.

The crystallized red pigment means a red pigment purified by the following steps. The purified red pigment includes, but not limited to, more than5% w/w, preferably between 10 to 70% w/w and more preferably between 20 to 50% w/w of proanthocyanidin (condensed tannin). Alternatively, the crystallized red pigment is more than5% w/w, preferably between 10 to 70% w/w, and more preferably between 20 to 50 w/w of purified proanthocyanidin (condensed tannin).

Further, preferably, the crystallized red pigment does not essentially include sugar (sugar chain) and/or carotenoid.

Crystallization means crystal form. The red pigment is a red material obtained from saw palmetto fruit. The methodology for purification is not limited, however, the red material includes anthocyanin, more preferably it includes proanthocyanidin (condensed tannin), and even preferably it is the crystallized red pigment as mentioned above.

Proanthocyanidin and condensed tannin are used synonymously. Proanthocyanidin (condensed tannin) is one in which catechin, epicatechin, epigallocatechin, afzelechin and others, contained widely in plants, is combined between a carbon and a carbon, or oligomer (preferably 2 to 10 monomers) to polymer (more than 11, preferably 11 to 50 monomers) of flavane. Proanthocyanidin (condensed tannin) generates anthocyanidin (aurantinidin, cyanidin,delphinidin, europinidin, luteolinidin, pelargonidin, malvidin, peonidin, petunidin, rosinidin etc.) by hydrolysis with hydrochloride.

Anthocyanidin means a moiety other than sugar or sugar chain (aglycon) of anthocyan which is a pigment widely existed in plants.

Proanthocyanidin (condensed tannin) in this invention includes a substance generating at least one selecting from cyanidin,delphinidin, peonidin, petunidin, malvidin when hydrated with hydrochloride. That is, it contains at least one substance selecting from procyanidin, prodelphinidin, propeonidin, propetunidin, promalvidin.

TABLE 1

Structures of representative anthocyanidin.

| anthocyanidin | $R^1$ | $R^2$ | $R^3$ | $R^4$ | $R^5$ | $R^6$ | $R^7$ |
|---|---|---|---|---|---|---|---|
| pelargonidin | H | OH | H | OH | OH | H | OH |
| cyanidin | OH | OH | H | OH | OH | H | OH |
| delphinidin | OH | OH | OH | OH | OH | H | OH |
| aurantinidin | H | OH | H | OH | OH | OH | OH |
| luteolinidin | OH | OH | H | H | OH | H | OH |
| peonidin | $OCH_3$ | OH | H | OH | OH | H | OH |
| malvidin | $OCH_3$ | OH | $OCH_3$ | OH | OH | H | OH |
| petunidin | OH | OH | $OCH_3$ | OH | OH | H | OH |
| europinidin | $OCH_3$ | OH | OH | OH | $OCH_3$ | H | OH |
| rosinidin | $OCH_3$ | OH | H | OH | OH | H | $OCH_3$ |

The crystal obtained is dried. Heat drying under low pressure is preferable. The drying temperature is, but not limited to, from room temperature to 80° C., preferably from 40 to 70° C. In the case of heated drying, the crystal becomes in the tar form. This crystal is readily soluble in ethanol, and produces a red ethanol solution.

A form of red pigment of saw palmetto fruit may be, but not limited to, a crystal form, an oily form after heated drying or an ethanol solution. Preferably, the red pigment is stored in a dark and at 4° C. A form of ethanol extract from saw palmetto fruit may be, but not limited to, dried oily form or ethanol solution.

The ethanol extract from saw palmetto fruit or the red pigment may be, but not limited to, a food, a cosmetic or a pharmaceutical. In addition, it may be a food additive, cosmetic additive or pharmaceutical additive. Similarly, a composition comprising the ethanol extract from saw palmetto fruit and the red pigment may be, but not limited to, a food, cosmetic or pharmaceutical. In addition it may be an additive in foods, cosmetics or pharmaceuticals.

An amount of the ethanol extract from saw palmetto fruit or the red pigment in a composition is, but not limited to, between 0.1 to 99.9% w/w, preferably between 1 to 99% w/w. Remaining moiety is a conventional carrier, excipient or additive etc.

A composition may further include a conventional carrier, excipient or additive etc. A conventional carrier, excipient or additive etc. may include a solvent, vegetable oil, mineral oil, fatty oil, liquid paraffin, buffer, preservative, moisturizer, chelating agent, anti- oxidant, stabilizer, emulsifier, suspending agent, gelling agent, ointment base, suppository base, penetrating agent, fragrance, sweetener, coloring agent, essences and skin protective agent etc.

A solvent includes, but not limited to, water, alcohol, BG (1,3-butylene glycol), polyethylene glycol, propylene glycol, glycerol, liquid polyalkylsiloxane and a mixture thereof.

A vegetable oil includes, but not limited to, almond oil, castor oil, cacao-seed oil, coconut-seed oil, corn oil, cottonseed oil, linseed oil, olive oil, palm oil, peanut oil, poppyseed oil, rapeseed oil, sesame oil, soybean oil, sunflower oil, wheat germ oil, rice oil, tea seed oil and mixtures thereof These oils may be purchased from a market or home production sources. Preferably, it is olive oil.

A buffer includes, but not limited to, citrate, acetate, tartrate, lactate, hydrogen phosphate, diethyl amine and mixture thereof A moisturizer includes, but not limited to, glycerin, propylene glycol, pentylene glycol, sorbitol, lactate, urea, BG (1,3-butylen glycol), soybean sterol and mixture thereof.

A chelating agent includes, but not limited to, sodium EDTA, citrate and mixture thereof.

An anti-oxidant includes, but not limited to, butyl hydroxyl anisole(BHA), ascorbate and its derivative, $\alpha$-,$\beta$-, $\gamma$-,$\delta$-tocopherol and its derivative, $\alpha$-,$\beta$-,$\gamma$-,$\delta$-tocotrierol and its derivative, cysteine and a mixture thereof.

A emulsifier includes, but not limited to, natural gum (e.g. acacia gum), tragacanth gum, xanthan gum; natural phosphatide (e.g. soybean lecithin); sorbitanmonooleate derivatives; wool grease; wool alcohol; sorbitan ester; mono glyceride; fatty alcohol (e.g. behenyl alcohol); fatty acid ester (i.e. tri(caprylic/capric acid)glyceryl, triglyceride of fatty acid like stearic acid glyceryl (SE); and a mixture thereof.

A suspending agent includes, but not limited to, a cellulose and its derivative (e.g. carboxymethyl cellulose, hydroxyethyl cellulose, hydroxypropyl cellulose, hydroxypropylmethyl cellulose etc.), carrageenan, acacia gum, tragacanth gum and a mixture of thereof.

A gelling agent and a thickeners includes, but not limited to, liquid paraffin, polyethylene, fatty oil, colloidal silica or aluminum, zinc soap, glycerol, propylene glycol, tragacanth, carboxyl vinyl polymer, magnesium-aluminum silicate, hydrophilic polymer, (e.g. starch, carboxymethulcellulose, hydroxyethcellulose and other cellulose derivative), water-swellable hydrocolloid, carrageenan, hyaluronan (e.g. hyaluronan gel selectively containing sodium chloride), alginate (e.g. alginate propylene glycol) and a mixture thereof.

An ointment bases includes, but not limited to, beeswax, paraffin, cetanol, cetylpalmitate, cetearyl alcohol, polyglyceryl (10) stearate, stearate, PEG (150) stearate, vegetable oil, sorbitan ester of fatty acid, poly ethylene glycol, condensation products of fatty acid sorbitan ester and ethylene oxide (e.g. monooleatepolyoxiethylenesorbitan) and a mixture thereof.

A hydrophobic ointment base includes, but not limited to, a paraffin, vegetable oil, animal fat, synthesized glyceride, wax, lanolin, liquid polyalkylsiloxane and a mixture thereof.

A hydrophilic ointment base includes, but not limited to, solid macrogol (PEG) etc. Further, conventional carriers, excipients and additives etc., includes squalane, lecithin, hydrogenatedlecithin, tetrahexydecanic acid ascorbyl, allantoin, dipotassium glycyrrhizinate, glycosyltrehalose, hydrolysis-hydrogenation starch, hydrolysis collagen, rose extract, dimethicone, capryl glycol, betaine, sodium stearoyl glutamate, wild rose oil, batyl alcohol and hydroxyproline etc.

Anti-angiogenesis means an effect of inhibiting or suppressing formation or growth of a new blood vessel. An anti-angiogenic agent means a composition having an anti-angiogenic action. An anti-angiogenic agent may be a food, cosmetic or pharmaceutical.

A disease or disorder benefit by suppressing angiogenesis means a disease or disorder in which the progression of the disease or the disorder is suppressed, or the symptom is improving or relieving, by suppressing angiogenesis, it includes, for example, cancer, retinopathy, glaucoma, macular degeneration, periodontal disease, psoriasis or arthritis. Preferably it is cancer, psoriasis or arthritis.

Psoriasis is preferably psoriasis vulgaris, psoriasis pustulosa, psoriasis arthoropathica or psoriasis guttata.

Arthritis is preferably osteoarthritis, arthritis of TMJ, rheumatic arthritis. More preferably, it is rheumatic arthritis with synovitis.

Retinopathy is preferably diabetic retinopathy and hypertensive retinopathy.

Glaucoma is preferably protopathic glaucoma, congenital glaucoma, secondary glaucoma and normotensive glaucoma.

Macular degeneration is preferably age-related maculopathy, preferably it is exudate type age-related maculopathy.

Periodontal disease is preferably gingivitis or periodontitis.

Cancer means a malignant tumor, preferably cutaneous cancer, lung cancer, breast cancer, stomach cancer, colorectal cancer, uterine cancer, ovarian cancer, laryngeal cancer, pharyngeal cancer, lingual cancer, osteosarcoma, chondrosarcoma, rhabdomyosarcoma, leiomyosarcoma, fibrosarcoma, liposarcoma, angiosarcoma, leukemia, malignant lymphoma, myeloma, hepatic carcinoma, cerebral cancer, renal cancer, esophageal cancer, prostatic cancer, testicular cancer, bladder cancer, oral cancer, thyroid cancer, pancreatic cancer, biliary cancer and head and neck cancer. Preferably it is skin cancer such as melanoma, breast cancer or hepatic cancer.

Cure means suppression of the development of disease or disorder, or improvement or reduction of the symptom. Prevention means prevention or delaying progression of the disease or disorder.

The subject for cure or prevention is preferably mammalian, for example, human, companion animal like the dog and cat, livestock such as bovine, swine or chicken. Preferably it is human.

Administration may be both systemic and topical administration. Systemic and topical administration may be dermal-, sublingual-, oral-, enteral-, intramuscular-, subcutaneous-, intravenous-, transnasal-administrations and instillation. Preferably it is dermal-, sublingual-, oral-, subcutaneous- of intravenous-administration.

The efficacy dose for cure or prevention of the disease or disorder depends on the extent of the disease or disorder, and the routes of administration. It is, but not limited to if it is an efficient dose of suppressing angiogenesis, 0.01 to 1000 mg/kg B.W./day, 0.1 to 1000 mg/kg B.W./day, preferably 1 to 500 mg/kg B.W./day, more preferably 10 to 100 mg/kg B.W./day of ethanol extract or red pigment from saw palmetto fruit.

The ethanol extract or red pigment from saw palmetto fruit may be used for manufacturing a medicine for the cure or prevention of the disease or disorder. A formulation of the medicine is, for example, a cream, sublingual tablet, massage oil, solution, suspension, lotion, ointment, gel, tablet, capsule, granule, powder, syrup, suppository. It is preferably a cream, sublingual tablet, massage oil, solution, tablet, capsule, granule or powder.

The composition may further contain other agent having anti-angiogenic action.

The present invention relates to a method of treat or prevention of the disease or disorder for which suppressing angiogenesis is beneficial, comprising administrating an effective dose of ethanol extract or red pigment from saw palmetto fruit to a mammal.

With over exposure of the skin to UV-rays, a thicker microvessel involved in wrinkle formation is increased abnormally. Therefore, the anti-angiogenic agent may be used for prevention or improvement of wrinkle formation. The anti-angiogenic agent may be a cosmetic for preventing or improving wrinkle. Thus, the ethanol extract or red pigment from saw palmetto fruit may be used for the production of a cosmetic for preventing or improving wrinkle.

Further, following examples illustrate the present invention. However, it should be understood that the present invention is not limited to the examples mentioned below.

EXAMPLE 1

Preparation of Purified Red Pigment of Saw Palmetto 1000 g of saw palmetto fruit (Saw Palmetto Berries Co-op of Florida Inc (SBP), 1206 King Way, Naples, Fla. 34112, USA) was milled using a mixer (Fiber mixer, Panasonic Corporation) then air dried to yield a dried weight of 886 g.

100 g of the milled and dried saw palmetto fruit was added to 1000 ml of 90% v/v ethanol in a stainless steel pressurized vessel (AS ONE Corporation) together with a magnetic stirrer bar. The stainless steel pressurized vessel was sealed and placed in a heated oil bath at 100° C. on a magnetic stirrer with a hot plate, and the contents are stirred for 1 hour at 400 rpm. The inner pressure of the vessel was 0.1 MPa compared to standard atmospheric pressure.

The vessel was removed from the oil bath and allowed to cool until the internal pressure returned to standard atmospheric pressure (the temperature is reduced at ca. 60° C.). The contents were then filtered through a 100 mesh nylon cloth (Kitamura Seifu Co. Ltd, pore size is 150 μm) and the residue was separated. 950 ml of the extract is fileted using filter aid (Celite , Celite 503) to prepare a primary coating. The primary coating was prepared by spreading 5 g of Ceolite on to filter paper (Advantec Toyo, No.2) laid on a Nutche suction filter (5 μm Sansyou).

Following filtration of the extract, the residue was further filtered with 50 ml of 90% v/v Ethanol with a yield of 1000 ml of filtrate. The 1000 ml of filtrate was concentrated to 100 ml volume using a vacuum evaporator (Tokyo Rika Kikai).

100 ml of the concentrate was added to 300 ml of distilled water in a 500 ml beaker (Shibata) and mixed using a magnetic stirrer at 400 rpm for 10 minutes at room temperature (23° C.).

After stirring, the beaker including the solution was placed in an ultrasonic cleaner (As One Corporation) and treated at 40 kHz for 1 minute. The extract separated into upper (oil) layer and a lower (water) layer. The lower layer contained the red crystalline precipitate.

The extract separating into oil layer and water layer was placed in a separating funnel. The water layer was recovered in a beaker, and filtered Using a separating funnel the water layer was separated. The crystalline material was then separated from the water using a Nutche suction filter (5 μm, Sansyou Corporation) overlaid a filter paper (Advantec Toyo Co. Ltd., No 2) under low pressure (8 kPa vs Absolute pressure) and then crystal is obtained on the filter paper. The wet filter paper was rinsed with water to remove remaining fat then the crystal was dried under reduced pressure (vacuum-constant temperature dryer, Advantec Toyo Co. Ltd.) at 60° C. 1.0 g of the red pigment of saw palmetto was obtained.

EXAMPLE 2

1. Measurement of the Anti-Angiogenic Activity of Purified Red Pigment Obtains from Saw Palmetto.

Following biological test results were conducted by Ricerca Bioscience, LLC (http://www.Ricerca.com.) under a contract (Assay#368000, Tumor, Angiogenesis, Tube Formation) with the crystalized red pigment prepared in Example 1.

Human umbilical vein endothelial cells (HUVEC) differentiate to capillary-like structures and form vessel network on Matrigel in the presence of endothelial cell growth supplements. The anti-angiogenic activity of a test compound can be assessed by observing continuity of vessel network compared with untreated control. Test compound (crystallized red pigment prepared in Example 3) was tested for an effect on anti-angiogenesis at five final concentrations of 100, 10, 1, 0.1 and 0.01 μg/mL.

2. Preparation of a Test Compound (Crystalized Red Pigment Prepared in Example 1)

The crystalized red pigment prepared in Example 1 was dissolved in 100% dimethyl sulfoxide (DMSO) and then diluted with sterile distilled water to obtain solutions of 1, 10, 100, 1000 and 10000 m/mL in 40% DMSO. The solutions were diluted 100-fold with culture medium to generate final concentrations of 0.01, 0.1, 1, 10 and 100 μg/mL.

3. Culture Method of Human Umbilical Vein Endothelial Cells (HUVEC)

HUVEC was purchased from American Type Culture Collection (ATCC CRL-1730). HUVEC cells were incubated in 5% $CO_2$ atmosphere of at 37° C. The culture medium used was Endothelial Cell Growth Medium supplemented with 10v/v % fetal bovine serum and 1% antifungal antibiotic.

4 Reagents: antifungal antibiotic (GIBCO BRL, USA), dimethylsulfoxide (Merck, Germany), endothelial cell growth medium (CELL APPLICATIONS, USA), fetal bovine serum (HyClone, USA), Matrigel matrix (BD Biosciences, USA) and Suramin (Sigma, USA).

5. Devices and Apparatus 96-microwell culture plate (NUNC, USA), Centrifuge 5810R (Eppendorf, Germany), Digital camera (Nikon, Japan), Hematocytometer (Hausser Scientific Horsham, USA), Inverted microscope CK-40 (Olympus, Japan), System microscope E-400 (Nikon, Japan) and Biological safety cabinet (NuAire, USA)

6. Methods

Matrigel matrix was thawed, kept on ice at 4° C. and 50μL of the matrix was transferred to each well of a 96-microwell culture plate. The plate was incubated at 37° C. for at least one hour to allow the matrix solution to solidify before treatment.

Aliquots of 2004 of HUVEC suspension (about $1.5 \times 10^4$ cells/well) were placed in the 96-well matrigel plate. Two microliters per well of test compound solution or vehicle (40% DMSO) was then added and incubated at 5% CO2, 37° C. for 18 hours (in duplicate). The final concentration of DMSO was 0.4%. The test compound was evaluated at concentrations of 100, 10, 1, 0.1 and 0.01 μg/mL. At the end of incubation, a tube network formed by endothelial cell in each wells was evaluated by photomicroscopy (magnification of 40×) and photographed. The total length of tube network was measured from each photograph (FIG. 1).

The reduction of the total length of tube network in test compound treatment to the total length of tube network in vehicle treatment control indicates anti-angiogenic activity. The minimum inhibitory concentration (MIC) and 50% inhibition concentration ($IC_{50}$) were determined to assess effect of the test substance on anti-angiogenesis.

Grant, D. S., Kinsella, J. L., Fridman, R., Auerbach, R., Piasecki, B. A., Yamada, Y., et al. Interaction of endothelial cells with a laminin A Chain peptide(SIKVAV) in vitro and induction of angiogenetic behavior in vivo. J. Cell Physiol.153:614-625, 1992. Belotti, D., Vergani, V., Drudis, T., Borsotti, P., Pitelli, M. R., Viale, G., Giavazzi, R. and Taraboletti, G. The microtubule-affecting drug paclitaxel has antiangiogenic activity. Clin. Cancer Res. 2:1843-1849, 1996.

7. Results

Figure 2:
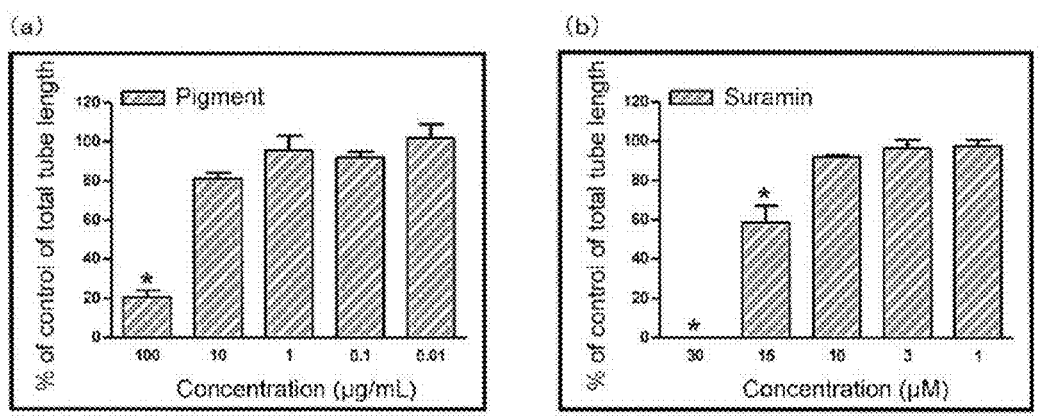
FIG. 2: Inhibition of red pigment for the tube formation. (a): the full length of formed tube treated with each concentration of red pigment ((a) to (e) of FIG. 1) is indicated as % of control, when the full length of formed tube in vehicle control ((f) of FIG. 1) is as 100%. Full length of the tube treated with 100 μg/mL of red pigment shows 20% of vehicle control and 10 μg/mL shows 80% of control. (b): the full length of formed tube treated with each concentration of suramin ((g) to (k) of FIG. 1) is indicated as % of control, when the full length of formed tube in vehicle control ((1) of FIG. 1) is as 100%. Full length of the tube treated with 30 μM of red pigment shows about 0% of vehicle control. Tube formation is completely inhibited by 30 μM of suramin treatment. *: remarkable inhibition of tube formation

Crystalized red pigment of the present invention at 100 μg/mL exhibited significant inhibition of tube formation relative to the vehicle-treated control. The standard reference reagent, Suramin, also exhibited significant inhibition at 30 and 15 $\mu M_{(Table}$ 2, FIGS. 1 and 2). The $IC_{50}$ value was shown in Table 3.

Inhibition of tube formation of red pigment of saw palmetto fruit

| Treatment | Assay Name | % Inhibition of total tube length (mean ± SEM) | | | | |
|---|---|---|---|---|---|---|
| | | Concentrations (μg/mL) | | | | |
| | | 100 | 10 | 1 | 0.1 | 0.01 |
| PT#1151525 Red Pigment | 368000, Angiogenesis Tube Formation | 80 ± 4[ab] | 19 ± 3 | 5 ± 8 | 8 ± 3 | −2 ± 7 |
| | | Concentrations (μg/mL) | | | | |
| | | 30 | 15 | 10 | 3 | 1 |
| Suramin | 368000, Angiogenesis Tube Formation | 100 ± 0[a] | 42 ± 9[ab] | 8 ± 1 | 4 ± 5 | 3 ± 4 |

[a]Significant inhibition of tube formation (30%)
[b]Minimum inhibitory concentration (MIC)

Inhibition of the tube formation for 70% or more relative to the vehicle-treated control group indicates significant anti-angiogenic activity.

Summary of Minimum Inhibitory Concentration (MIC) and $IC_{50}$

| Treatment | Assay # | Assay Name | MIC | $IC_{50}$ |
|---|---|---|---|---|
| PT#1151625 Red pigment | 368000 | Tumor, Angiogenesis, Tube Formation | 100 μg/mL | 32 μg/mL |
| Suramin | 368000 | Tumor, Angiogenesis, Tube Formation | 15 μM | 16 μM |

EXAMPLE 3

A composition containing the red pigment from saw palmetto fruit as the following formulation was prepared.

| Ingredient | Blending quantity of cream (% w/w) |
|---|---|
| Ethinoic extract or red pigment from saw palmetto | 2.0 |
| Olive oil | 10.0 |
| Tri (capryl/capric acid) glyceryl | 10.0 |
| Tocopherol | 1.0 |
| D.W. | 77.0 |
| Total | 100.0 |

EXAMPLE 4

Measurement of proliferation inhibition activity of VEGF-Induced cell of vascular endothelial cells by purified red pigment from Saw palmetto.

Following results of a biological test was conducted by Ricerca Bioscience, LLC (http://www.Ricerca.com.) with the crystalized red pigment prepared in Example 1.

Test Compounds and Doses

The test compounds, NYG-1, DS-SMO, SMO and AK were evaluated for a study of EGF proliferation. These compounds were dissolved and diluted in 100% DMSO and concentrations were adjusted to 2.63 mg/mL and 26.3 mg/mL with DMSO.

The final concentration in the test was given as 100 μg/mL and 10 μg/mL.

NYG-1: Crystalized red pigment prepared in Example 1.

DS-SMO: Lipophilic fraction extracted by ethanol from deep sea shark meat

SMO: Lipophilic fraction extracted by ethanol from shark meat

AK: Concentrated alkoxy glyceryl (AKG) of shark liver oil

Cells and Media

HUVEC (human umbilical vein endothelial cells) were purchased from American Type Culture Collection (ATCC CRL-1730). HUVEC cells were incubated in air atmosphere of 5% $CO_2$ at 37° C. The culture medium used was Endothelial Cell Growth Medium with 10% fetal bovine serum (FBS). The medium for assay was M199 medium supplemented with 10% FBS and 10 μg/mL of Heparin.

Reagents

Dimethyl sulfoxide (Merck, Germany), Endothelial cell growth medium (CELL APPLICATIONS, USA), Fetal bovine serum (HyClone, USA), Heparin (Sigma, USA), SU5416 (Calbiochem, USA), $VEGF_{165}$ (Calbiochem, USA) and HBSS(Gibco, USA)

Devices and Apparatus 96-microwell tissue culture plate (NUNC, USA), Centrifuge CT6D (Hitachi, Japan), Nucleocounter (ChemoMetec, Denmark), Inverted microscope CK-30 (Olympus, Japan) and Biological safety cabinet (NuAire, USA)

Methods

Aliquots of HUVEC ($1.1 \times 10^5$ cells/ well) were pre-seeded in the 96-well TC plate in an incubator at 5% $CO_2$, 37° C. Test compound solution or vehicle (DMSO) was then added per well and incubated at 5% $CO_2$, 37° C. for 20 minutes. Thereafter, VEGF$_{165}$ (0.2 nM) was added and incubated for 48 hours. 48 hours later, the cells were washed with HBSS once. Then 5 μg/mL of the fluorescence reagent, CalceinAM dye (BD Biosciences, USA) was added and incubated for another 50 minutes. After incubation, fluorescence intensity was detected by Micro plate reader. More than 50% of suppression for VEGF$_{165}$ induced proliferation was indicated for the significant antagonistic activity of the test reagent.

Summary of Methos
307900 Cell proliferation, VEGF-Induced

| Target: | Human | Quantitation Method | Spectrofluorimetric quantitation of cell proliferation |
|---|---|---|---|
| Vehicle: | 0.4% DMSO | Signif. Criteria Ag.: | ≥50% Increase in proliferation relative to VEGF$_{165}$ response |
| Incubation Time/Temp: | 2 days @ 37° C. | Signif, Criteria Ant.: | ≥50% Inhibition of VEGF$_{165}$ induced proliferation |
| Incubation buffer | M199 Medium, 10% FBS, 10 μg/mL Heparin, pH 7.4 | | |

Results

The results were shown in the following Table5. NGY-1 (red pigment from saw palmetto) shows antagonistic activity. 100 μg/mL (final conc.) presents remarkable antagonistic activity (140%).

From the above, it is demonstrated that the red pigment from saw palmetto can suppress proliferation, activation and angiogenesis of VEGF induced cell in vascular endothelial cells.

EXAMPLE 5

Anti-tumor Activity of the Red Pigment from Saw Palmetto (A) The red pigment from saw palmetto suppressed human hepatocarcinoma in the heterograft of nude mouse model.

Materials

NYG-1, Red pigment from saw palmetto (Crystallized red pigment prepared in Example 1)

Carcinoma cell line: Human hepatocarcinoma cell line MHCC-97L (the Liver Cancer Institute of Fudan University (Shang Hai, China))

Heterograft Model: Nude Mouse

Methods $1\times10^5$ of MHC-97L cells (Human hepatocarcinoma cell line) were inoculated subcutaneously into the right side of the nude mouse. One week later, 0.1 mg/kg and 1 mg/kg of NYG-1 were administered by intraperitoneal injection into the mice. NYG-1 was injected in the same way one time each week for 3 weeks. Thereafter, mice were sacrificed at day 25 and solid tumors were extirpated. The size of each tumor was scaled by the Vernier caliper, after the last treatment of NYF-1 and the tumor growth curve was drawn.

TABLE 5

Summary of AK, DS-SMO, NYG-1 and SMO activities

| Cat# | Assay Name | Batch | Spec. tissue | Rep. | Conc | Criteria Resp | Ag. | Ant. | R |
|---|---|---|---|---|---|---|---|---|---|
| Compound: 307900 | AK, PT#: 1154011 Cell proliferation, VEGF-induced | 305353 | hum hum | 2 2 | μg/mL 100 10 | ≥50% ≥50% | ND ND | 12% 2% | |
| Compound: 307900 | DS-SMO,PT#: 1154009 Cell proliferation, VEGF-induced | 305353 | hum hum | 2 2 | μg/mL 100 10 | ≥50% ≥50% | ND ND | 14% 0% | |
| Compound: 307900 | NYG-1, PT#: 1151625 Cell proliferation, VEGF-induced | 305353 | hum hum | 2 2 | μg/mL 100 10 | ≥50% ≥50% | ND ND | 140% 30% | |
| Compound: 307900 | SMO, PT1154010 Cell proliferation, VEGF-induced | 305353 | hum hum | 2 2 | μg/mL 100 10 | ≥50% ≥50% | ND ND | 14% 1% | |

The result of IC$_{50}$/EC$_{50}$ was shown in the following Table 6. The IC$_{50}$/EC$_{50}$ value of red pigment from saw palmetto was calculated at 0.12 μM. SU5416 is a known anti-angiogenesis agent (antagonist).

TABLE 6

IC$_{50}$/EC$_{50}$

| Cat# | Assay Name | Ref. Comp. | Hist IC$_{50}$/ EC$_{50}$ | Concurrent Batch | IC$_{50}$/ EC$_{50}$ |
|---|---|---|---|---|---|
| 307900 | Cell proliferation, VEGF-induced-Ant | SU5416 | 0.48 μM | 305353 | 0.12 μM |

The tumor size was calculated as follows; Scaling the minor and major axis by Vernier caliper, then calculated as (minor axis)$^2$ *major axis/2.

MHCC-97L cells were incubated in air atmosphere of 5% CO$_2$ at 37° C. The culture medium used was DMEM (GIBCO, USA) supplemented with 10% v/v heat-inactivated fetal bovine serum and 100IU/mL penicillin G and 100 m/mL streptomycin.

Results

Figure 3:
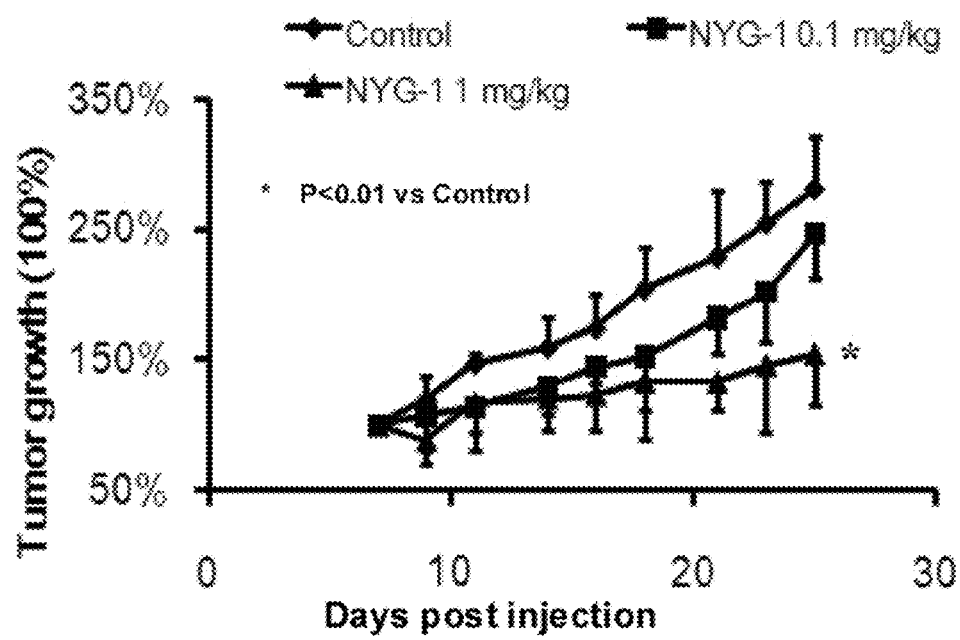
FIG. 3: Anti-tumor effect of red pigment from saw palmetto (A): Tumor growth curve of human hepatocellular carcinoma on the heterograft nude mouse model. "NYG-1 0.1 mg/kg" and "NYG-1 1 mg/kg" mean that saw palmetto pigment in saline is administrated intraperitoneally at amount of 0.1 mg or 1 mg per 1 kg of body weight, respectively. "Control" is saline only. "Day post injection" means the period of the day after the last injection (day 0). "Tumor growth (%)" was calculated by using the tumor size of "day 7" as 100% of each group (Control, NYG-1 0.1 mg/kg and NYG-1 1 mg/kg). (B): Suppressed VEGF expression of human hepatocellular carcinoma on the heterograft nude mouse model. "VEGF expression (%)" means an amount of vascular endothelial growth factor (VEGF) in a supernatant after centrifugation of tumor homogenate.
Figure 3:
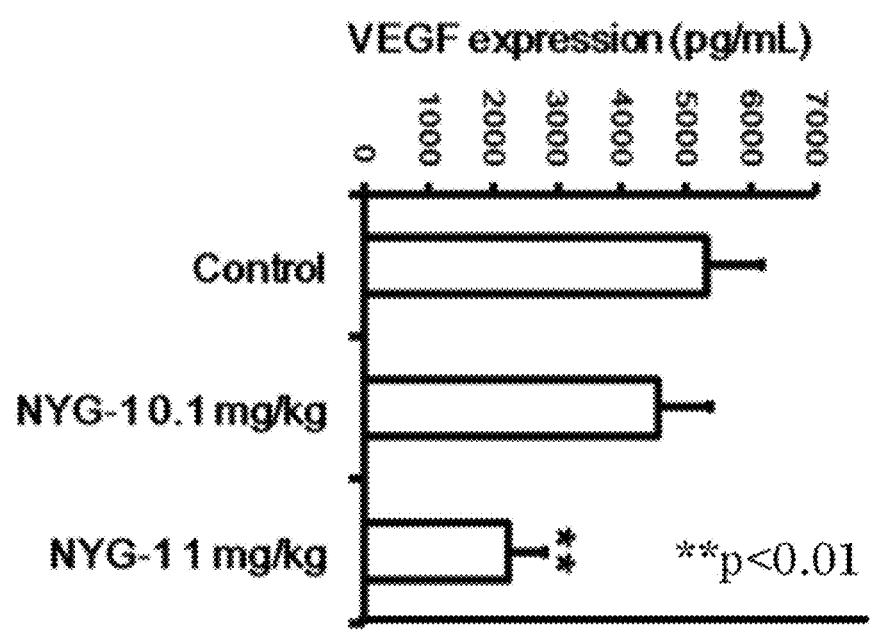

As shown in FIG. 3 (A), in NYG-1 treatment group, tumor growth of the heterograft mouse model was suppressed in a dose-dependent manner. In particular the group with 1 mg/mL of NYG-1 suppressed the tumor growth (about 50% of control, P<0.01).

(B) The red pigment from saw palmetto suppressed VEGF expression in human hepatocarcinoma in the heterograft nude mouse model.

The tumor sample of above mentioned (A) after scaling was homogenized and centrifuged. And then, the amount of vascular endothelial growth factor (VEGF) in human hepatocarcinoma was measured by ELISA assay.

Results

As shown in FIG. 3(B), in NYG-1 treatment group, the expression of vascular endothelial growth factor (VEGF) in human hepatocarcinoma in the heterograft nude mouse model was suppressed in a dose-dependent manner In particular, the group with 1 mg/mL of NYG-1 inhibited the VEGF activity, more than 40% of the control group (P<0.01).

EXAMPLE 6

A composition containing the red pigment from saw palmetto fruit as the following formulation was prepared.

| Ingredient | Formulation (mg/tablet) |
| --- | --- |
| Red pigment or ethanolic extract | 50 |
| Lactose | 110 |
| Microcrystalline cellulose | 30 |
| Silica ($SiO_2$) | 5 |
| Talc | 5 |
| Final weight | 200 |

EXAMPLE 7

A test was conducted to identify pigment components of the purified red pigment from saw palmetto in Example 1.

According to HANDBOOK of Phytochemical Constituents of GRAS Herbs and Other Economic Plants (1992, JAMES A, DUKE), β-carotene and tannins are indicated as pigment components of the saw palmetto to date. Therefore, there is a possibility that polyphenol compounds such as flavonoid as well as above-mentioned two kinds of compound would be pigment components of the saw palmetto. A validation test for the above mentioned three kind of compound was carried out to identify the substance.

A) Validation test for carotenoid compounds

Any carotenoid compounds were not detected by thin layer chromatography (TLC) and high performance liquid chromatography (HPLC).

B) Validation test for tannins.

(1) Validation test by ferric chloride III solution

Ferric chloride III solution (dissolved 9 g of $FeCl_3.6H_2O$ in 100 mL of water) produced a green-brown color. Therefore, it is suggested that the pigment possibly contained condensed tannin (proanthocyanidin). In this test, the green-brown color indicates condensed tannin (proanthocyanidin) and a blue to dark blue color indicates hydrolysised tannin.

(2) Validation Test by Vanillin-hydrochloride Solution

Vanillin-hydrochloride solution (dissolved 0.5 mg vanillin in 0.5 mL of ethanol (95%), and added 0.5 mL of water and 3 mL of HCl) produced an orange color. Therefore, the pigment possibly contained tannin A red to orange color in this test indicates tannin.

(3) Validation Test of Condensed Tannin (Proanthocyanidin) by TLC (I)

Under the detection condition for catechin orooligo-proanthocyanidin (di- to tetramer) of TLC, the spot indicated only the starting point. Therefore, the pigment possibly contains the higher polymerized condensed tannin (proanthocyanidin).

(4) Validation Test of Condensed Tannin (Proanthocyanidin) by TLC (II)

Figure 4:
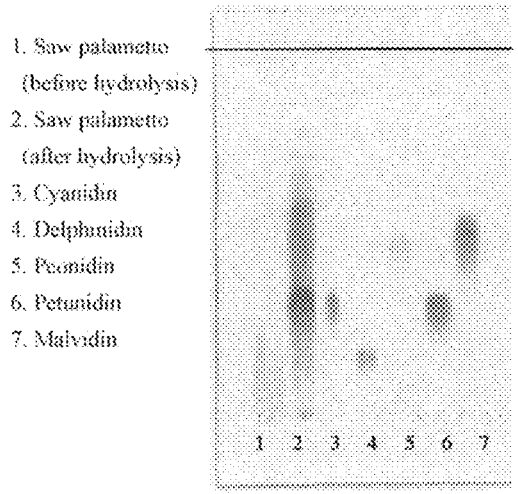
FIG. 4: TLC analysis of purified saw palmetto red pigment. Lean1: Purified saw palmetto red pigment (Before hydrolysis), Lean2: Purified saw palmetto red pigment (After hydrolysis), Lean3: cyanidin(standard), Lean4: delphinidin (standard), Lean5: peonidin (standard), Lean6: petunidin (standard), Lean7: malvidin (standard). Cellulose TLC glass plate (Merck) is attached an airtight container, at room temperature, with acetate: hydrochloride: water=30:3:10 as the developing solvent. The plates were analyzed visually.
Figure 5:
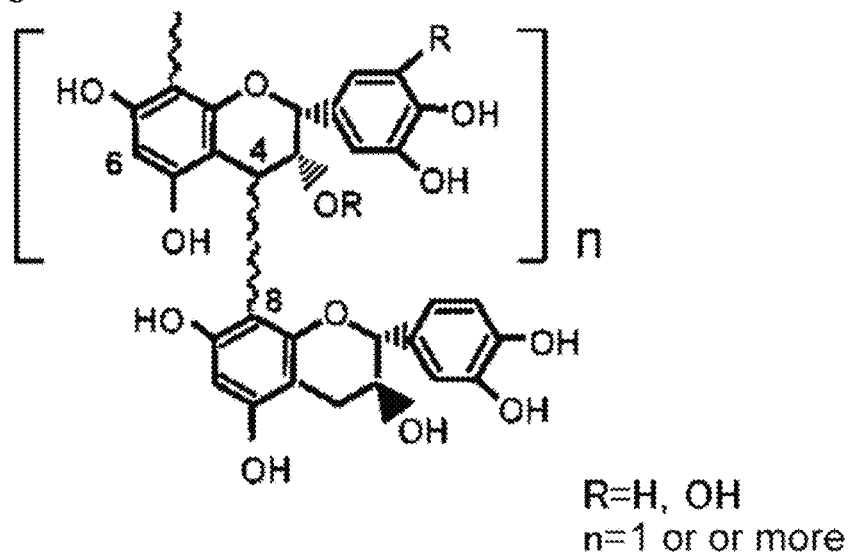
FIG. 5: Structural formula of proanthocyanidin from grape (condensed tannin) as an embodiment of proanthocyanidin (condensed tannin)

The pigment pretreated by acid hydrolysis (added HCl and maintained 80° C. in a water bath for 30 minutes). The hydrolysate indicated a clear red color, suggesting that anthocyanidin may have been generated. The hydrolysate analyzed by TLC, gave the spot for anthocyanidin, therefore the original (i.e. before hydrolysis) pigment includes proanthocyanidin (FIG. 4).

Results

The above-mentioned data suggests that the purified red pigment from saw palmetto contained no carotenoids, but contained higher, polymerized condensed tannin (proanthocyanidin).

EXAMPLE 8

Assay for Poly Phenol Content

Total poly phenol content was measured by using Folin Ciocalteu reagent.

Measuring Method 25 mg of purified red pigment from saw palmetto in application 1, was dissolved in 100 mL of 50% V/V ethanol, and diluted 4 times with distilled water, and a 2 mL sample placed in a test tube. Then added 2 mL of Folin Ciocalteu solution diluted twice with distilled water, and stirred. After 3 minutes, added 2 mL of 10% w/v sodium bicarbonate ($NaHCO_3$) solution and agitated at 25° C. for 60 minutes. After that, the absorbance at 655 nm was determined by spectrophotometer. The standard curve was prepared for a series of dilutions of catechin solution. Thereafter the equivalent of catechin content (mg/100 g) as the total poly phenol content was calculated.

Results

The total poly phenol content of the purified red pigment from saw palmetto was 30 to 40% w/w, by analysis.

The other component of the red pigment other than poly phenol, was considered to be the existence of residual fat.

EXAMPLE 9

Figure 6:
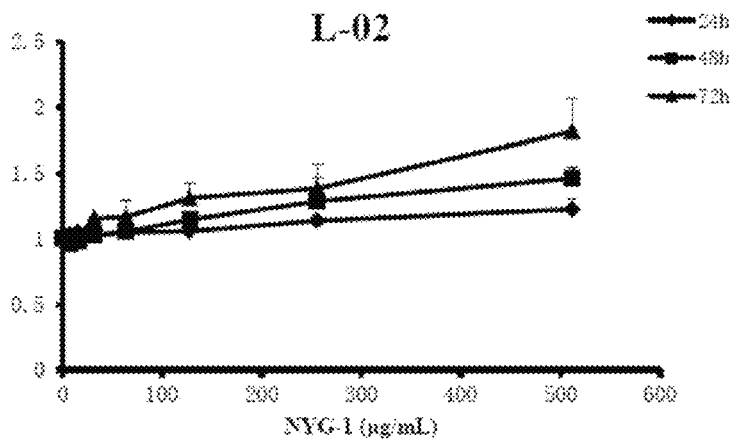
FIG. 6: Cytotoxicity of NYG-1 on a normal hepatocyte. The longitudinal axis is absorbance at 595 nm/Ref 650 nm, and it is indicated as % of control.

Whether NYG-1 indicates cytotoxicity to normal hepatocyte was tested. The effect of NYG-1 on the growth of L-02 cells was tested by using hepatocyte cell line L-02. NYG-1 induced the cell growth of normal hepatocyte in a dose- and time-dependent manner (FIG. 6).

EXAMPLE 10

Figure 7:
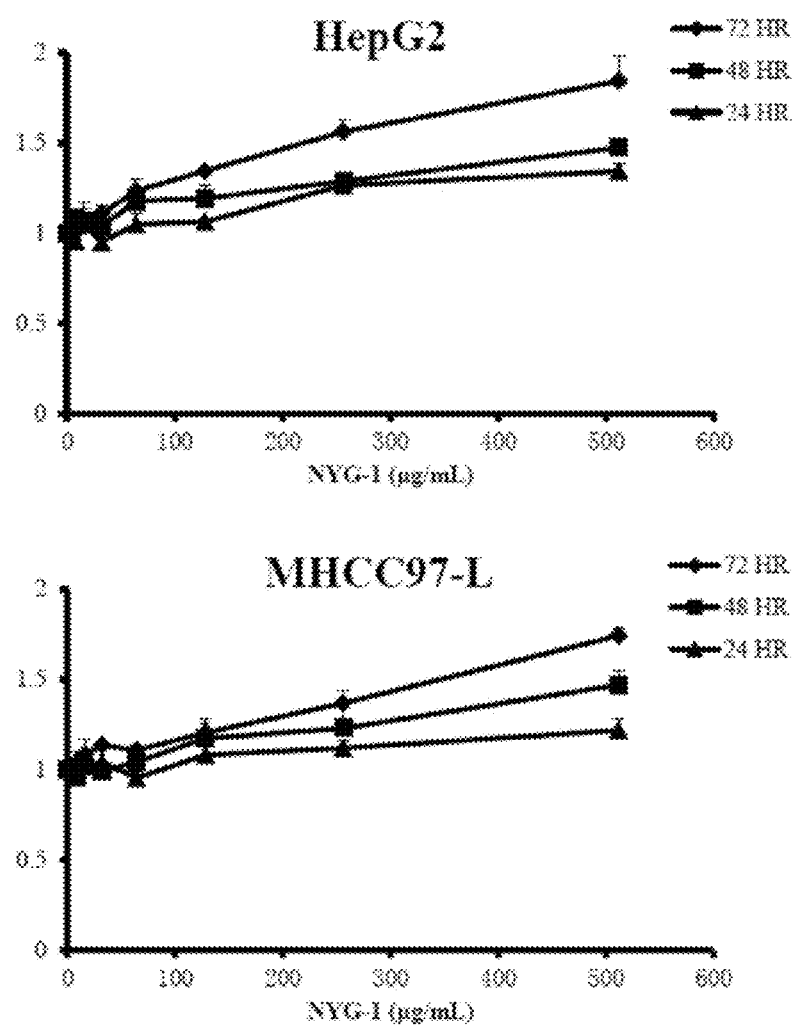
FIG. 7: Effect of NYG-1 on the growth of HCC cells (HepG2 and MHC97L). The longitudinal axis is absorbance at 595 nm/Ref 650 nm, and it is indicated as % of control.

Whether NYG-1 indicates anti-growth effect on hepatocellular cancer (HCC) was tested. Two major hepatocellular cancer cell lines, HepG2 and MHCC97L were used. In a high dose, NYG-1 stimulated the growth of HCC cells (FIG. 7). When HCC cells were treated with NYG-1 at doses more than 100 μg/mL, a significant increase of HCC growth was observed.

EXAMPLE 11

Figure 8:
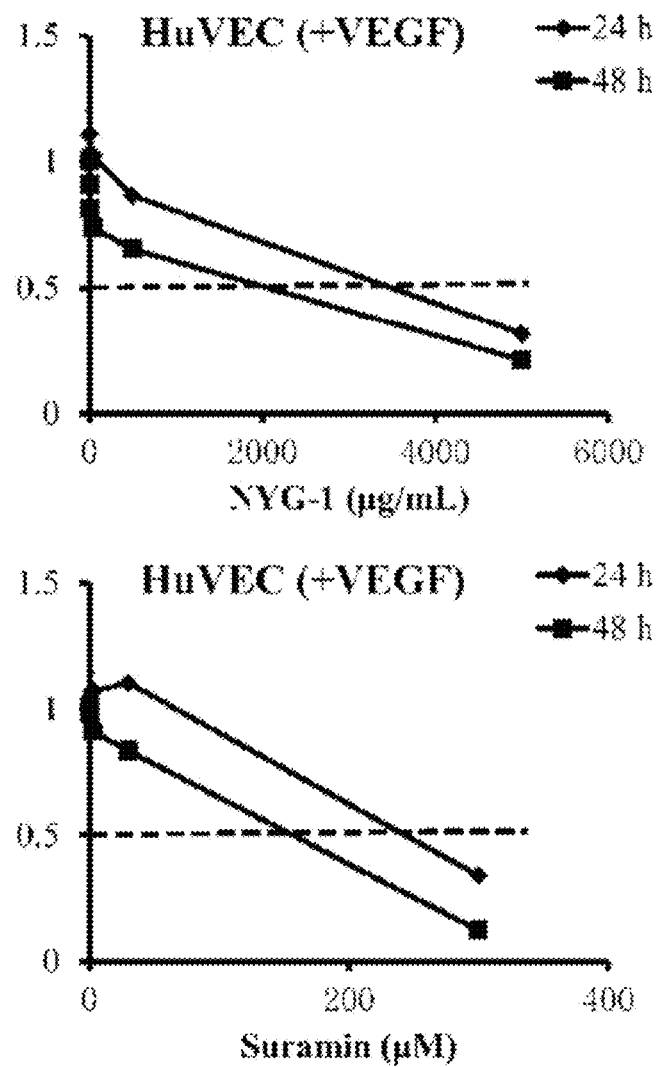
FIG. 8: Cytotoxicity of NYG-1 and suramin on a vascular endothelial cell. The longitudinal axis is absorbance at 595 nm/Ref 650 nm, and it is indicated as % of control.

The stimulating effect of NYG-1 on HCC cells was observed, and then, whether NYG-1 can suppress growth, migration and invasion of vascular endothelial cells was validated. The growth activity of cells under exposure to NYG-1 was detected by using HuVEC cells which is an in vitro cell model. In contrast to normal cells or HCC cells, NYG-1 did not induce the growth of HuVEC cells. Contrastingly, strong cytotoxicity was observed at high dose NYG-1 treatment, the doses showing cytotoxicity of NYG-1 were rather high than the doses that NYG-1 can induce the growth of HCC cells or hepatocytes. Further, suramin was used as a positive control. Suramin showed strong cytotoxicity at a few hundred micro mole level. This level was higher than the dose inducing dysfunction of HuVECs (FIG. 8).

EXAMPLE 12

Figure 9:
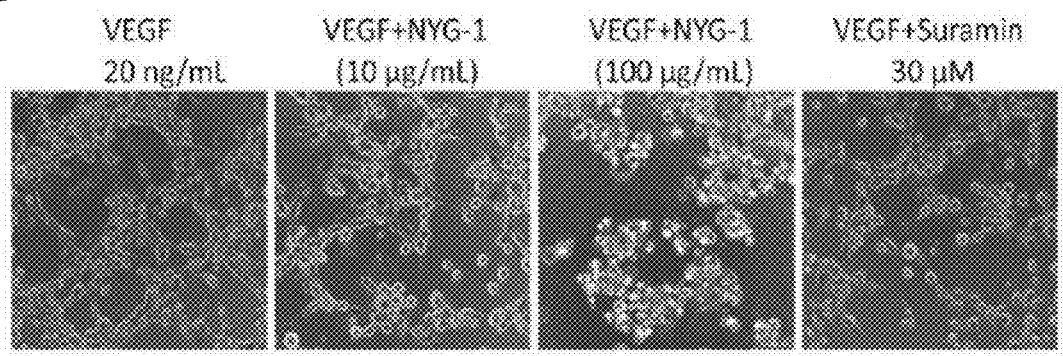
FIG. 9: NYG-1 suppresses angiogenesis at low dose.

In turn, whether NYG-1 can suppress angiogenesis ability of HuVECs was tested. In the presence of VEGF, NYG-1 at low dose significantly suppress the tube formation of HuVECs cells. The treatment of NYG-1 at 10 µg/mL was enough for the inhibition of blood vessel formation. As for high doses, 100 µg/mL of NYG-1 treatment also inhibited blood vessel formation. Suramin as a positive control can suppress blood vessel formation at 30 µM not showing cytotoxicity (FIG. 9).

EXAMPLE 13

Figure 10:
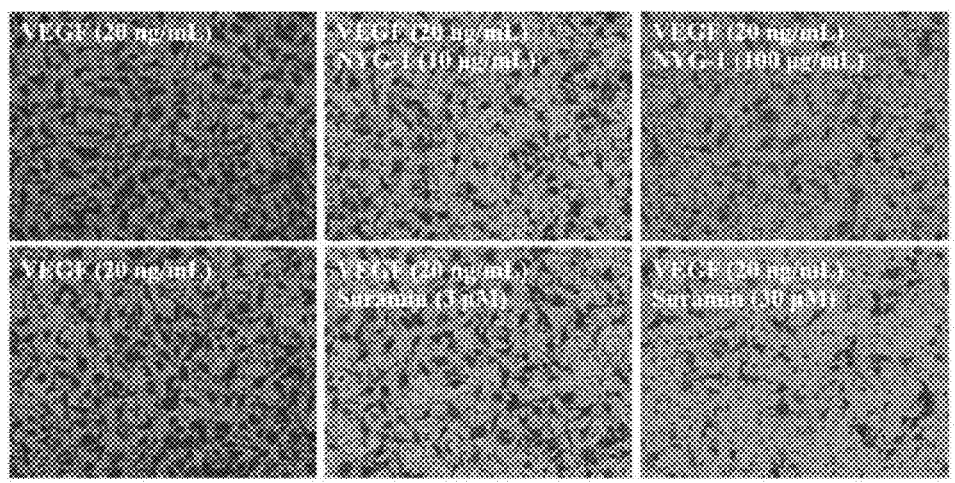
FIG. 10: NYG-1 suppresses migration of HuVECs.

It is demonstrated that migration of HUVECs by VEGF plays a key role in the angiogenesis ability. Whether low dose treatment of NYG-1 can suppress cell motility in HuVECs was tested by using a Transwell for monitoring cell migration. NYG-1 inhibited cell migration at non-toxic and non-tumor-stimulatory doses. Similarly, sumiran showed the similar effect at 30 µM (FIG. 10).

EXAMPLE 14

Figure 11:
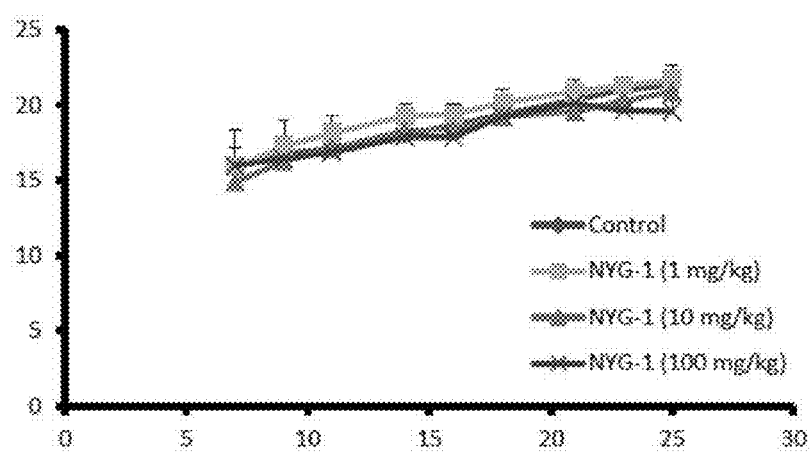
FIG. 11: Monitoring of body weight of a mouse treated by NYG-1. The longitudinal axis is body weight (g) and the horizontal axis is days.

Anti-tumor effect of NYG-1 in vivo was investigated since there is inconsistency between the stimulatory effects on tumor cell growth at high dose and the inhibitory effects on blood vessel formation at low dose, from the information of ability for suppressing cell migration and blood vessel formation of HuVECs by NYG-1. Dose escalation study using HCC xenografting animal model was set for the purpose of obtaining an optimum dose for anti-HCC effect of NYG-1. Whether NYG-1 at 1, 10, 100 and 1000 mg/kg have dose-depending anti-tumor effect was tested. NYG-1 treated mouse (1000 mg/kg, i.p.) was dead on the day after the first administration. This showed that 1000 mg/kg of NYG-1 has strong toxicity to mouse. NYG-1 treatment at low dose showed no adverse side effect in mouse as shown by normal body weight in the treated mouse (FIG. 11).

Figure 12:
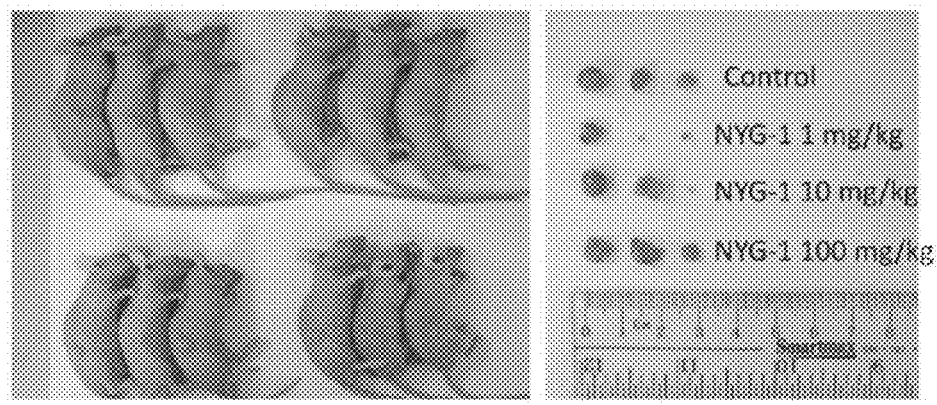
FIG. 12: NYG-1 at low dose can suppress a tumor growth in a heterologous transplantation model.

Three weeks later, the mouse was sacrificed and a tumor was extirpated. A significant inhibition of tumor growth was observed in the mouse treated with 1 mg/kg of NYG-1. Interestingly, no significant inhibition anti-tumor effect was observed in 10 mg/kg and 100 mg/kg of NYG-1 (FIG. 12).

From the information, the possibility of pharmaceutical action of NYG-1 is as follows:
(1) NYG-1 has an anti-HCC effect by inhibiting a process of blood vessel forming of a tumor;
(2) The effect of NYG-1 is different depend on dose. NYG-1 at low dose can suppress tumor growth by suppressing blood vessel formation, although NYG-1 at high dose has a stimulating effect on HCC cell growth and it does not show significant effect;
(3) Suppression of blood vessel formation by NYG-1 depends on an inhibitory effect on migration of vascular endothelial cells by VEGF.

EXAMPLE 15

Figure 13:
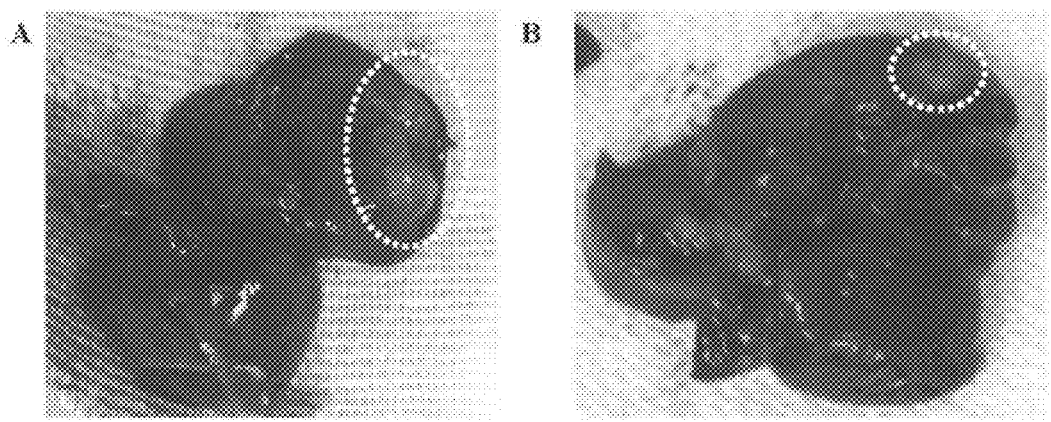
FIG. 13: NYG-1 reduces the tumor size in a orthotropic liver tumor transplantation mouse. A is non-treated, and B is NYG-1 treated.

Tumor volume of a NYG-1 treated mouse is decreased compared to a non-treated mouse. Two groups of mouse were treated for five weeks with or without NYG-1 (n=3). The extirpated liver was measured and significant decrease in tumor volume was observed in NYG-1 treated mouse (FIG. 13).

EXAMPLE 16

Figure 14:
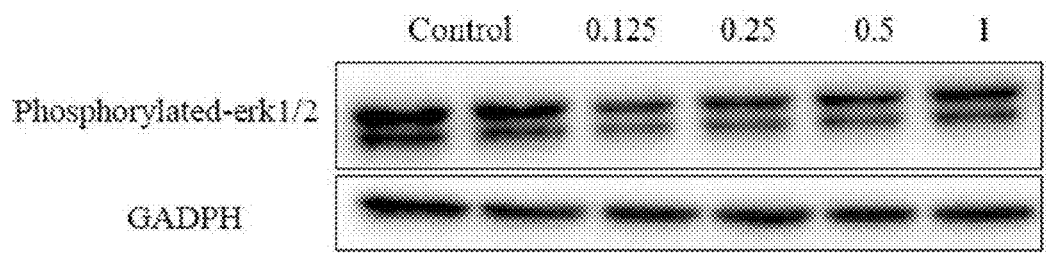
FIG. 14: NYG-1 induces a phosphorylation of Erk1/2 in HepG2.
Figure 15:
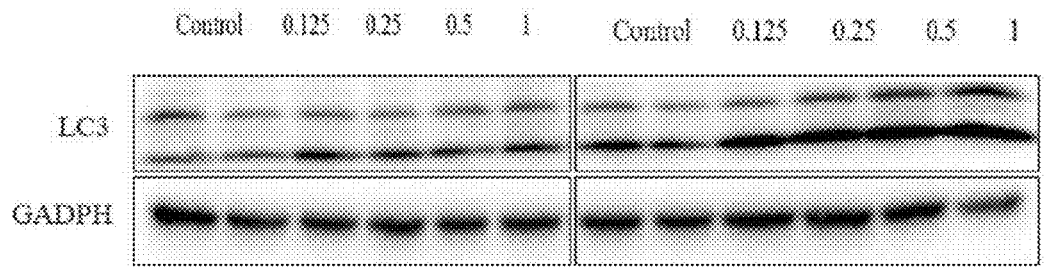
FIG. 15: NYG-1 induces a phosphorylation of Erk1/2 in HepG2. Left-hand column is normal oxygen conditions and right-hand column is low oxygen conditions.

A downstream protein target of VEGFR in NYG-1 mediated HepG2 was investigated by Western blot. NYG-1 induced Erk1/2 phosphorylation in HepG2. HepG2 cells were treated with NYG-1 (0, 0.125, 0.25, 0.5, 1 mg/ml). Cell lysate was immunobloted to anti-pErk1/2 and GADPH. The expression of phosphorylated Erk1/2 was down-regulated and it showed inhibition of Erk1/2 activation in HepG2 after NYG-1 treatment. Erk1/2 is an extracellular regulated kinase and it plays a central role regarding apoptosis and cell survival (FIG. 14).

EXAMPLE 17

NYG-1 induces an expression of LC3 which is autophagy marker, in HepG2 cells. HepG2 cells was treated with NYG-1 (0, 0.125, 0.25, 0.5, 1 mg/ml). Cell lysate was immunobloted to anti-LC3 and GADPH. The expression of was up-regulated and it showed LC3 activation in HepG2 after NYG-1 treatment. LC3 is a microtubule relating protein and it used for monitoring autophagy.

INDUSTRIAL APPLICABILITY

An ethanol extract or red pigment from saw palmetto fruit of the present invention has angiogenesis activity, and useful for treatment or prevention of wide-ranging various diseases. These diseases include angiogenesis-related diseases such as psoriasis, arthritis, retinopathy, glaucoma, macular degeneration, periodontal disease and cancer. Further, the present invention is useful for prevention or improvement of wrinkles.

The invention claimed is:
1. A method for treating a human suffering from liver cancer comprising administering a therapeutically effective amount of a crystallized red pigment of saw palmetto fruit to the human suffering from liver cancer, said crystallized red pigment of saw palmetto fruit having been obtained by a process comprising:
  conducting an extraction of saw palmetto fruit with ethanol, thereby obtaining an extract of saw palmetto fruit and a solid residue;
  separating the extract of saw palmetto fruit from the solid residue;
  concentrating the extract of saw palmetto fruit to form a concentrated extract of saw palmetto fruit;
  mixing the concentrated extract of saw palmetto fruit with water to form a mixture of saw palmetto fruit and water;
  ultrasonicating the mixture of saw palmetto fruit and water to separate a water layer from an oil layer; and
  recovering the crystallized red pigment of saw palmetto fruit from the water layer, wherein the administration of the crystallized red pigment of saw palmetto fruit to the human in need thereof effectively treats the liver cancer in the human in need thereof.
2. The method of claim 1, wherein said crystallized red pigment of saw palmetto fruit contains proanthocyanidins.

* * * * *